United States Patent
Yeung et al.

(10) Patent No.: US 8,444,682 B2
(45) Date of Patent: May 21, 2013

(54) SHAPE MEMORY LOCKING DEVICE FOR ORTHOPEDIC IMPLANTS

(75) Inventors: Kelvin Wai Kwok Yeung, Tai Wai (HK); William Weijia Lu, Hong Kong (HK); Keith Dip Kei Luk, Pokfulam (HK); Kenneth Man Chee Cheung, Mid-Levels (HK)

(73) Assignee: The University of Hong Kong, Hong Kong (HK)

( * ) Notice: Subject to any disclaimer, the term of this patent is extended or adjusted under 35 U.S.C. 154(b) by 1250 days.

(21) Appl. No.: 11/853,686

(22) Filed: Sep. 11, 2007

(65) Prior Publication Data

US 2008/0065074 A1  Mar. 13, 2008

Related U.S. Application Data (60) Provisional application No. 60/844,237, filed on Sep. 13, 2006.

(51) Int. Cl.
*A61B 17/86* (2006.01)

(52) U.S. Cl.
USPC ........................... 606/305; 606/78

(58) Field of Classification Search
USPC ........................... 606/78, 305–308
See application file for complete search history.

(56) References Cited

U.S. PATENT DOCUMENTS

| | | | |
|---|---|---|---|
| 5,167,626 A * | 12/1992 | Casper et al. ............. | 604/891.1 |
| 5,496,321 A * | 3/1996 | Puno et al. ............. | 606/305 |
| 5,540,689 A * | 7/1996 | Sanders et al. ............. | 606/276 |
| 6,160,084 A | 12/2000 | Langer et al. | |
| 6,210,413 B1 | 4/2001 | Justis et al. | |
| 6,254,602 B1 | 7/2001 | Justis | |
| 6,388,043 B1 | 5/2002 | Langer et al. | |
| 6,720,412 B2 | 4/2004 | Donoho et al. | |
| 2003/0127413 A1 * | 7/2003 | Spinelli et al. .............. | 215/11.4 |
| 2005/0080325 A1 * | 4/2005 | Erickson ...................... | 600/395 |
| 2005/0154390 A1 * | 7/2005 | Biedermann et al. .......... | 606/61 |
| 2005/0277927 A1 * | 12/2005 | Guenther et al. .............. | 606/61 |
| 2007/0171609 A1 * | 7/2007 | Kehl et al. ...................... | 361/690 |
| 2008/0033431 A1 * | 2/2008 | Jung et al. ...................... | 606/61 |

OTHER PUBLICATIONS

Balabaud et al., "Biomechanical Evaluation of a Bipedicular Spinal Fixation System: A Comparative Stiffness Test," *Spine* 27(17):1875-1880(2002).

(Continued)

*Primary Examiner* — Eduardo C Robert
*Assistant Examiner* — Julianna N Harvey
(74) *Attorney, Agent, or Firm* — Pabst Patent Group LLP (57) ABSTRACT

A mechanism to connect the supporting portions of orthopaedic implants such as in the head, spine, upper limb and lower limb and thereby prevent loosening and fretting at the implant interface of an orthopaedic implant construct has been developed based on shape memory effect and superelasticity of shape memory materials such as nickel-titanium (nitinol or NiTi) shape-memory-alloy, without the use of typical threaded fastening technique. Advantages are conferred by making the entire device, not just connecting pieces, out of shape memory alloy and having shape memory effect and super-elasticity. Heating the memory head of the device will compress the connection portion without the use of an auxiliary device (e.g. coupling member) so that the connection portion can be completely clamped down by the memory head. Further advantages are provided through the use of a two-way shape memory effect in which the memory device can be closed or tightened by heating up the ambient temperature, and re-opened by cooling down the temperature.

18 Claims, 5 Drawing Sheets

OTHER PUBLICATIONS

Bullmann, et al., "Dual-Rod Correction and Instrumentation of Idiopathic Scoliosis with the Halm-Zielke Instrumentation," *Spine* 28(12)1306-1313(2003).

Glazer et al., "Biomechanical Analysis of Lumbosacral Fixation," *Spine* 21(10):1211-1222 (1996).

Kasai, et al., "Metal Concentrations in the Serum and Hair of Patients With Titanium Alloy Spinal Implants," *Spine* 28(12):1320-1326(2003).

Kotani et al., "Static and Fatigue Biomechanical Properties of Anterior Thoracolumbar Instrumentation Systems: A Synthetic Testing Model," *Spine* 24(14)1406(1999).

Liu, et al., "Criteria for pseudoelasticity in near-equiatomic NiTi shape memory alloys," *Acta Materialia* 45(11):4431-4439(1997).

Liu, et al., "Criteria of transformation sequences in NiTi shape memory alloys," *Materials Transactions* 37(4):691-696(1996).

Liu, et al., "Two-way shape memory effect developed by martensite deformation in NiTi," *Acta Materialia* 47(1):199-209(1999).

Magerl "Stabilization of the Lower Thoracic and Lumbar Spine with External Skeletal Fixation,"*Clinical Orthopaedics* 189(10):125-41(1984).

Senaran, et al. "Ultrastructural Analysis of Metallic Debris and Tissue Reaction Around Spinal Implants in Patients With Late Operative Site Pain," *Spine* 29(15):1618-1623(2004).

Stanford et al., "Multiaxial Pedicle Screw Designs: Static and Dynamic Mechanical Testing," *Spine* 29(4):367-375(2004).

Wang, et al. "Metal Debris From Titanium Spinal Implants," *Spine* 24(9):899(1999).

Yeung, et al., "Optimization of thermal treatment parameters to alter austenitic phase transition temperature of NiTi alloy for medical implant," *Materials Science and Engineering A* 383(2):213-218(2004).

\* cited by examiner

SHAPE MEMORY LOCKING DEVICE FOR ORTHOPEDIC IMPLANTS

CROSS-REFERENCE TO RELATED APPLICATIONS

This application claims priority to U.S. Ser. No. 60/844,237 filed Sep. 13, 2006. The disclosure in the application listed above is herein incorporated by reference.

FIELD OF THE INVENTION

The present invention relates to a mechanism for connecting two or more implant members using shape-memory technology. In one embodiment, the present invention relates to a mechanism for connecting a spinal rod and a bone member in a spinal fixation system.

BACKGROUND OF THE INVENTION

The primary objective of orthopaedic instrumentation is to maintain anatomical alignment of bone segments by sharing the loads acting on the bone, usually until bone fusion takes place. Current orthopaedic implant memory locking devices are variations of a design, in which some kind of nut is used to lock the supporting portion into the head of a bone anchor to form a coupling. For instance, in spinal instrumentation, various fastening mechanisms such as threaded fasteners or rivet fasteners have been used to secure facilitate securement of bone anchors to the connective structures. These components provide necessary stability both in tension and compression to achieve immobilization. However, it is well known that the threaded fastener can loosen under the influence of cyclic loadings that are commonly encountered by the spinal column. Therefore, the mechanical stability of the spinal implant can degrade. Also, wear between the supporting portion and the memory locking device (called fretting) is expected, which generates particulate debris that are considered to be associated with post-operation complications such as implant-induced osteolysis, pseudarthrosis, subacute low-grade implant infection, late operative site pain and abnormal metal concentration in serum. See, for example, Bullmann, et al., Spine 2003; 28(12):1306-1313; Wang, et al., Spine May 1, 1999; 24(9):899; Senaran, et al., Aug. 1, 2004; 29(15):1618-1623; and Kasai, et al., Spine 2003; 28(12):1320-1326.

U.S. Pat. Nos. 6,210,413 and 6,254,602 disclose shape memory locking devices for use in orthopedic repair. The mechanism of their locking devices depends on the interaction of compression member (20 in FIG. 1 of '602 and 24a and 24b in FIG. 2 of '413) and locking member (22 in FIG. 1 of '602 and 26a and 26b in FIG. 2 of '413). Only these two members are made of shape memory alloy and have shape memory effect and super-elasticity. The compression member and locking member generate a locking force to push the coupling member (18 in FIG. 1 of '602). Heating the locking and compression members tightens the coupling and connecting portions. However, there is no means of releasing the portions or retightening the connection materials formed of materials such as nickel-titanium (nitinol or NiTi) shape-memory-alloy, without the use of typical threaded fastening technique.

The shape-memory phenomenon is that a material can exhibit one shape at a cold temperature and another shape after being heated to a higher temperature; see Liu, et al., Materials Transactions 1996; 37(4):691-696. The material is in its original shape at the higher temperature. When being cooled to a lower temperature, the material retains its original shape but changes the structure to martensite (stable phase at the lower temperature), where the material can be easily deformed into different shapes at the lower temperature. Upon heating, the material changes back to austenite (stable phase at the higher temperature), where the deformation is recovered and the shape is restored (one-way shape memory). Alloys can also have two memories (two-way shape memory) that exhibit a reversible effect, with heat causing the change in shape which can be reversed by cooling; see Liu, et al. 1996; Liu, et al., Acta Materialia 1999; 47(1):199-209.

Super-elasticity (SE) or is a property that the material can exhibit a constant recovery force when it is under deformation at a temperature at or above the austenitic phase transition temperature. See Liu, et al., Acta Materialia 1997; 45(11):4431-4439.

It is therefore an object of the present invention to provide mechanisms for connecting orthopedic devices, specifically spinal fixation systems, which are stable and less likely to produce particulate debris.

It is a further object of the invention to provide mechanisms for connecting orthopedic devices which can be tightened, released, and reconnected in situ without the use of a coupling member It is a still further object of the present invention to provide shape memory devices in orthopaedics that can prevent loosening and fretting at the implant interface after implantation.

SUMMARY OF THE INVENTION

A mechanism to connect the supporting portions of orthopaedic implants such as in the head, spine, upper limb and lower limb and thereby prevent loosening and fretting at the implant interface of an orthopaedic implant construct has been developed based on shape memory effect and super-elasticity of shape memory materials such as nickel-titanium (nitinol or NiTi) shape-memory-alloy, without the use of typical threaded fastening technique. The shape-memory phenomenon is that a material can exhibit one shape at a cold temperature and another shape after being heated to a higher temperature. The material is in its original shape at the higher temperature. When being cooled to a lower temperature, the material retains its original shape but changes the structure to martensite (stable phase at the lower temperature), where the material can be easily deformed into different shapes at the lower temperature. Upon heating, the material changes back to austenite (stable phase at the higher temperature), where the deformation is recovered and the shape is restored (one-way shape memory).

Advantages are conferred by making the entire device, not just connecting pieces, out of shape memory alloy and having shape memory effect and super-elasticity. Heating the memory head of the device will compress the connection portion without the use of an auxiliary device (e.g. coupling member) so that the connection portion can be completely clamped down by the memory head. By eliminating the coupling device, this should provide larger and more even compression force across the connecting portion. Further advantages are provided through the use of a two-way shape memory effect in which the memory device can be closed or tightened by heating up the ambient temperature, and re-opened by cooling down the temperature. The locking and unlocking temperatures are adjustable with the use of a heat treatment protocol. Further, the memory head has a re-tightening effect in which the head further clamps down the connecting portion if wearing/fretting occurs at the interface of the head and the connecting portion. This specific function may attribute to the super-elasticity of shape memory alloy and is also manipulated by the own heat treatment protocol.

For example, in spinal applications, this memory locking device can automatically clamp the spinal rod into position once the mechanism is heated to the austenite phase transition starting temperature or above. If the mechanism is cooled down to below the austenite phase transition starting temperature, the memory locking device can be then released automatically. The supporting portions of the memory locking device can be further tightened if the super-elasticity occurs to help prevent loosening and fretting at the implant interface of the implant construct. The locking temperature is adjustable by using various methods such as thermal treatment and thermal mechanical treatment. The memory locking device can be triggered by heating via direct contact, indirect contact or remote means. The memory locking device can prevent the loosening and fretting at the implant interface of orthopaedic implant construct such as spinal rod in spinal instrumentation. The tightening process is triggered automatically, when its ambient temperature reaches the austenite phase transition starting temperature. If loosening occurs, a re-tightening effect is initiated by the mechanism automatically, thereby saving the mechanical stability of the implant as a whole. The re-tightening effect can also reduce and/or prevent wear debris generation from the fretting at the implant interface in order to minimize post-surgical complications associated with impwith implant wear debris.

The memory locking device can also be used with other internal or external surgical implantations.

In the preferred embodiment, the shape memory locking device makes use of shape memory effect and super-elasticity of nickel-titanium alloys can prevent the loosening and fretting at the implant interface of orthopaedic implant constructs such as spinal rods in spinal instrumentation. The tightening process can be triggered automatically, when its ambient temperature is reached to austenite phase transition starting temperature. Moreover, if loosening occurs, a re-tightening effect will be initiated by the mechanism automatically so as to save the mechanical stability of the implant in whole. This phenomenon can be seen if the ambient temperature is beyond the austenite phase transition starting temperature of the mechanism made of shape memory materials. In addition, the re-tightening effect can also reduce and/or prevent wear debris generation from the fretting occurring at the implant interface in order to minimize post-surgical complications associated with implant wear debris.

The applications of this memory locking device are not limited to spinal surgical implants, but also apply to other internal or external surgical implantations such as in head, spine, lower limb and upper limb implants.

The memory locking device can be made of any metal or polymer having shape memory effect and super-elasticity. When alloy is used, the alloy is preferably a shape memory alloy comprising nickel and titanium. Preferably, the nickel titanium shape memory alloy substantially comprises nickel and titanium. More preferably, the alloy comprises 10%-90% of titanium together with balanced nickel volume. The ratio of nickel to titanium preferably is in the range of 1:9-9:1, 2:8-8:2, 3-7-7:3, 4:6-6:4, or 5:5. Alternatively, the alloy is a nickel free shape memory alloy comprises other metallic and non-metallic elements that are able to perform shape memory effect and super-elasticity.

In one embodiment, the locking device includes the concept of low-profile design to prevent or reduce the implant protrusion after surgical implantation. Alternatively, the locking device may include a side-opening and therefore the implanted portion can be captured from the side. In another embodiment, the locking device may include an undercut at the bottom or side wall of the locking device in order to release the locking device.

The locking force of the locking device can be varied by adjusting the composition of the alloy, e.g., the content of nickel and titanium. Also, the locking force can be varied by different thermo-treatment, thermo-mechanical treatment, radiation treatment, ternary alloying, and any combination thereof. The treatments are normally under oxygen and pressure controlled environment. Alternatively, the locking force can be varied by adjusting the diameter, height, dimension, base thickness of the locking device. The locking process is triggered by the means of direct or indirect heating, such as by conduction heating or the use of electromagnetic radiation. The locking/unlocking temperature of the locking device is adjustable by varying the composition of the alloy, e.g., the contents of nickel and titanium. It can also be varied by different thermo-treatment, thermo-mechanical treatment, radiation treatment, ternary alloying, and any combination thereof Usually, the treatments are under oxygen and pressure controlled environment. The locking/unlocking of the device can be triggered by any change of ambient temperature. The locking device can be locked by itself if the ambient temperature reaches the assigned locking temperature. It can be released if the ambient temperature reaches the assigned unlocking temperature. The locking temperature represents the austenite phase transition starting temperature. The locking temperature means temperature above the austenite phase transition stating temperature. The unlocking temperature means any temperature that is below the austenite phase transition starting temperature.

DETAILED DESCRIPTION OF THE INVENTION

Memory locking devices designed to connect the supporting portions of orthopaedic implants are able to prevent loosening and fretting at the implant interface of orthopaedic implant construct. The memory locking device can be designed for use with any internal or external surgical implantations. It can be applied to orthopaedic applications such as in head, spine, lower limb and upper limb.

Design of Memory Locking Device

The devices are designed from known designs for use as prosthetic implants for orthopedic repair. These are modified as described below to use the shape memory materials.

Figure 1A:
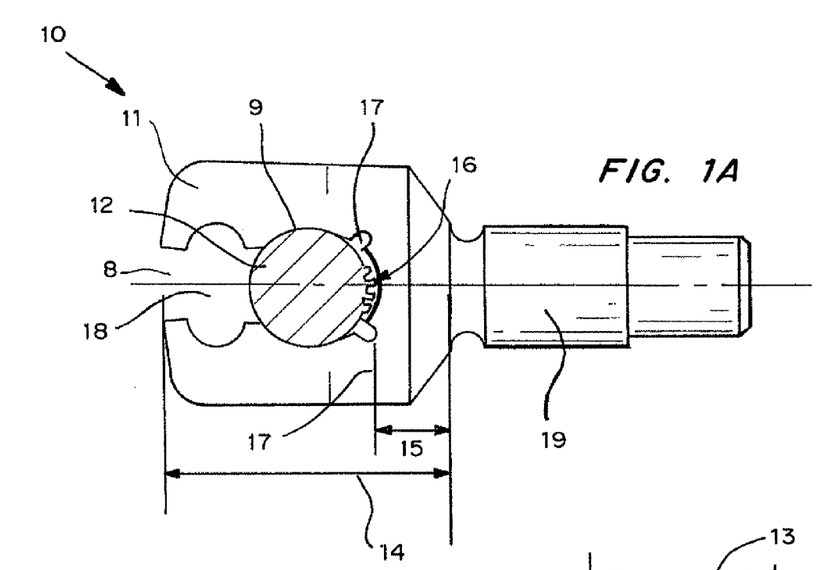
FIG. 1A is a front plan view of one embodiment of a memory locking device as described herein.
Figures 1B, 1C:
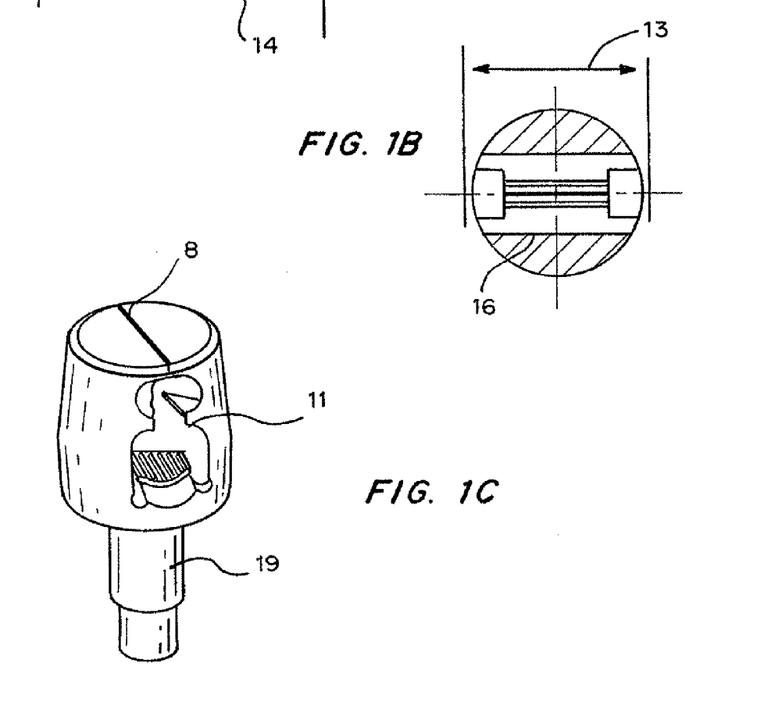
FIG. 1B is a cross-sectional view of the holding member of the memory locking device.
FIG. 1C is a perspective view viewed from the top-opening of the shape memory locking device according to another embodiment described herein.

FIG. 1A depicts a memory locking device 10 according to a preferred embodiment of a memory locking device 10. The memory locking device 10 includes a holding member 11 and a stem 19. In this embodiment, the stem 19 has a length of about 15 mm and diameter of about 5 mm, at the bottom of the holding member 11. The holding member 11 is in a shape of a cylinder as shown in FIG. 1C and has a height 14 of about 14 mm and a thickness 15 of about 4 mm. The holding member 11 defines a hole 9 around the central location for holding a spinal rod 12 that is implanted into human bone. The hole 9 has a diameter of about 6 mm. Preferably, the holding member 11 further defines a top-opening 18 in connection with hole 9. The cross-section of the top opening 18 is in a substantially round (with a diameter of about 2 mm) or oval shape (with the radius of internal circle being about 1 mm) and may includes a slit 8 having a width of about 1.3 mm for inserting an opening device so as to open the holding member extending through the top of the holding member 11. The top-opening 18 allows insertion of a tool to expand the hole 9 so that the spinal rod can be fitted into the hole 9. In a typical application, the hole 9 further includes a spline 16 at the other side of the hole 9, i.e., opposite to the top-opening 18, to enhance the mechanical stability of the holding member 11 and the security of the held spinal rod 12. The hole 9 may further include two recesses 17 at each side of the spline 16 to facilitate the expansion of the hole 9. The cross-section of each recess 17 is basically in a half-round shape with a radius of about 0.5 mm.

The locking strength of the memory locking device 10 can be varied by adjusting diameter 13, i.e., the diameter of the holding member 11, and the thickness 15 of the holding member 11, as shown in FIG. 1B. In a preferred embodiment, the diameter 13 is about 12 mm and thickness 15 is about 4 mm.

Figure 2A:
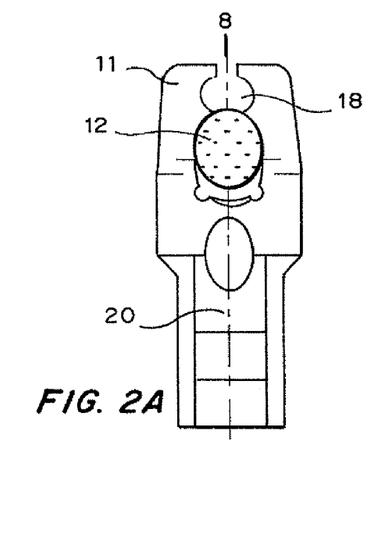
FIG. 2A is a front prospective view of a portion of another embodiment of the memory locking device.
Figure 2B:
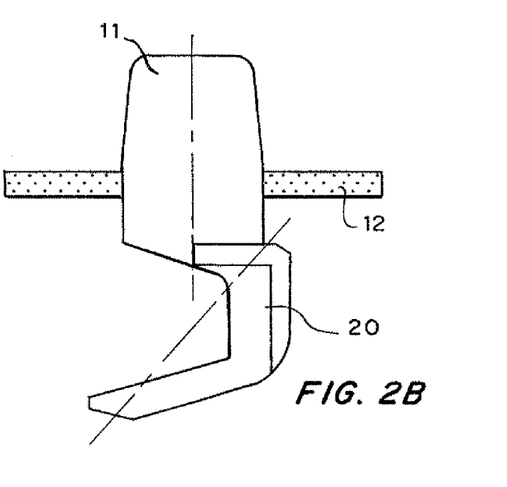
FIG. 2B is a side view of a portion of a memory locking device according to another embodiment of the shape memory locking device.
Figure 2C:
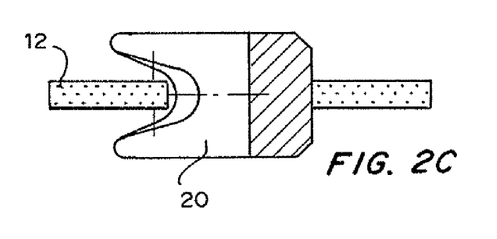
FIG. 2C is an enlarged cross-sectional side view of the stem of a memory locking device made into an anchor according to another embodiment of shape memory locking device.
Figure 3A:
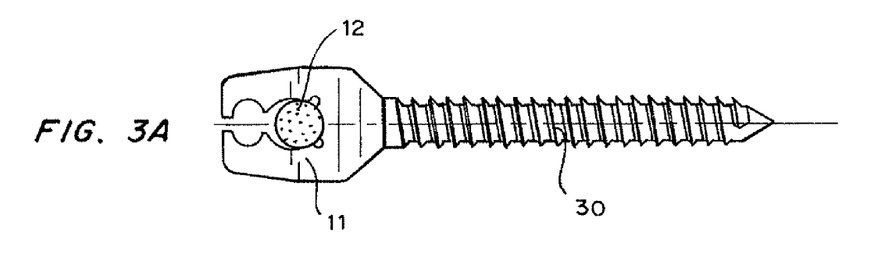
FIG. 3A is a front prospective view of another embodiment of a memory locking device described herein.
Figure 3B:
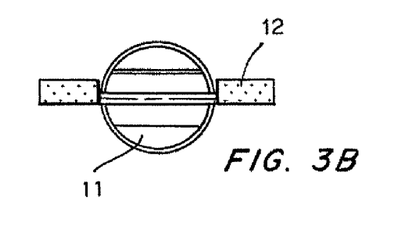
FIG. 3B is a cross-sectional view of the memory locking device according to another embodiment of the shape memory locking device described herein.

The stem 19 of the memory locking device 10 can be formed into or combined with different kinds of bone anchors or bone engaging fasteners. As shown in FIGS. 2A-2C, the stem is formed into an anchor 20 having a length of about 13 mm. As shown in FIG. 3A, the stem is formed into a screw 30. Alternatively, the stem can be formed into any kinds of connectors such as rod, shaft, wire etc. for connecting with different kinds of bone anchors.

Figure 4A:
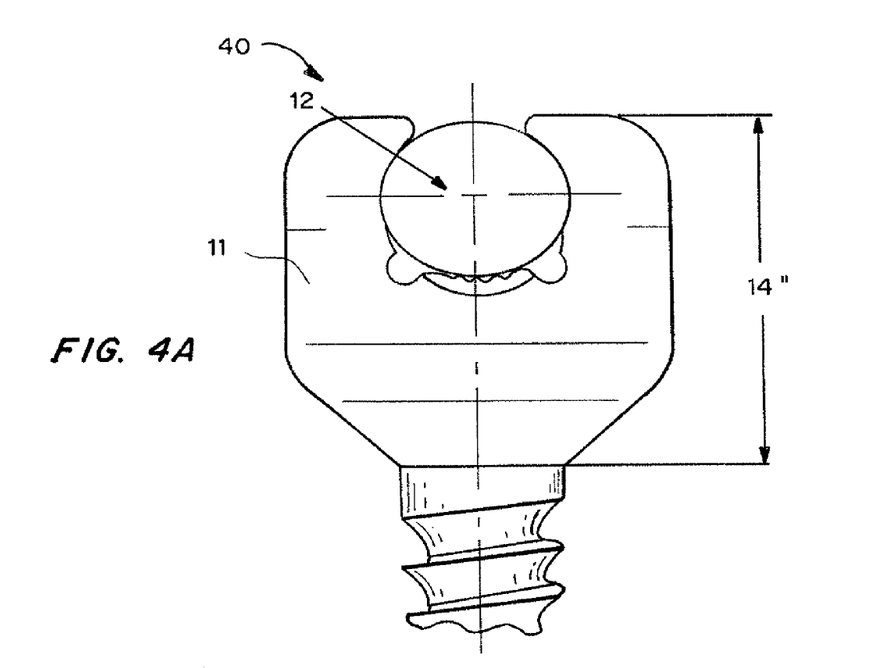
FIG. 4A shows a front perspective view of a portion of a low-profile full-rod capturing memory locking device.
Figure 4B:
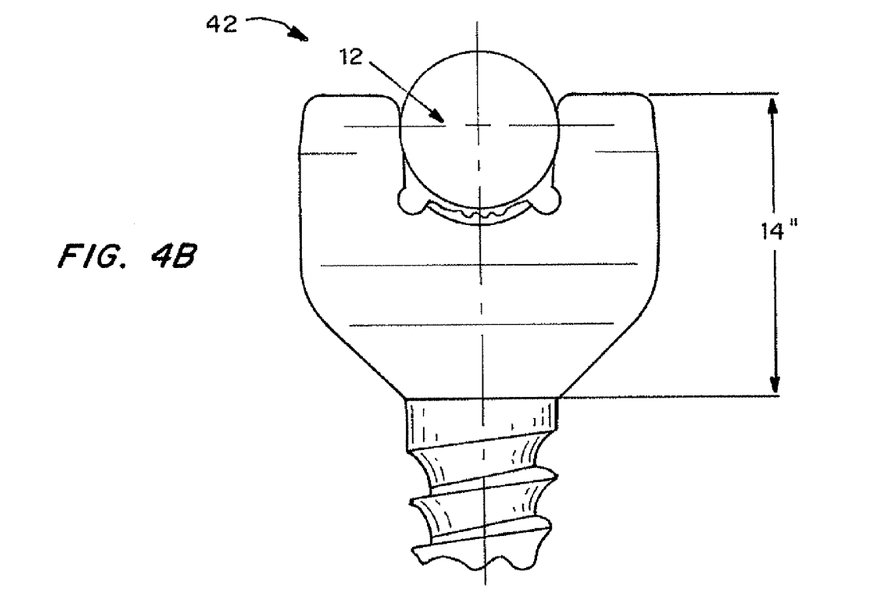
FIG. 4B shows a front perspective view of a portion of a low-profile half-rod capturing memory locking device.

The memory locking device can be made with a low profile design wherein the height 14 of the holding member is reduced to such an extent that the top-opening 18 is absent and a portion of the hole is exposed to the outside of the holding member. FIG. 4A depicts a low-profile full rod capturing memory locking device 40, wherein the height 14" of the holding member 11 is merely sufficient to capture at least the 4/5 of the entire circumference of the implanted spinal rod 12. FIG. 4B depicts a low-profile half rod capturing memory locking device 42, wherein the height 14" of the holding member 11 is further reduced such that only 2/3 of the circumference of the implanted spinal rod 12 can be captured. Reducing in the height of the holding member 11 helps to prevent or reduce the protrusion of the orthopaedic implants to the skin of the patients. Therefore, the patients will not feel uncomfortable after implantation because of implant protrusion.

The drawings here only show the designs for full-rod capturing and half-rod capturing, but similar designs can be used to capture various portions of the circumference of the implanted rod 12 such as one-half circumference or three-fourths circumference.

Figure 5:
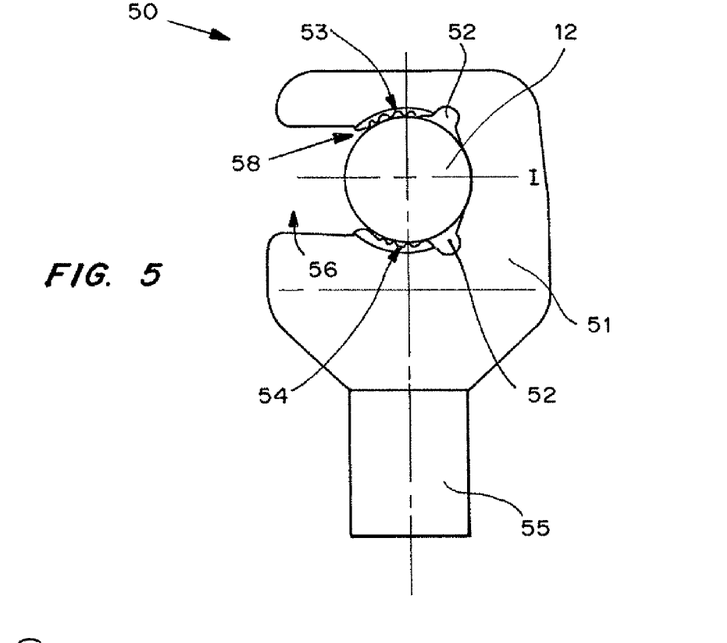
FIG. 5 shows a front plan view of a portion of a side-open memory locking device.

FIG. 5 shows the design of a side-open memory locking device 50. The side-open memory locking device 50 has a holding member 51 defining a hole 58 and an axis L about which it is generally symmetrical. A side opening 56 is disposed at one side of the hole 58 for capturing implants such as the spinal rod 12. At the other side of the hole 58, two recesses 52 are disposed at opposite sides of the axis L whereby the holding member 51 can be opened as wide as possible. An upper spline 53 and a lower spline 54 are disposed at each side of the side opening 56 to enhance the security of the captured implant. The stem 55 can be formed into or combined with different kinds of bone anchors such as hook and screw, or any connector for connecting with bone anchors.

It is understood that while the holding member of the devices as illustrated are in the shape of a cylinder, other shapes of holding members can also be adopted, such as rectangular column, hexagonal column, oval column or any other shapes envisioned by those skilled in the art. It is also understood that the dimensions given in the description are merely illustrations of specific embodiments and can be varied according to the needs by those skilled in the art.

Materials for Forming Devices

The memory locking device can be made of any alloy, polymer, or shape memory materials having shape memory effect and super-elasticity. There are two general classes of materials that can be used to make the devices, shape memory metal alloys and polymers.

Shape memory allows are known and well characterized. See, for example, Liu et al. Materials Transactions 1996; 37(4):691-696; Liu et al. Acta Materialia 1999; 47(1):199-209; Liu, et al., Acta Materialia 1997; 45(11):4431-4439; and Yeung, et al., Materials Science and Engineering A 2004; 383(2):213-218. When alloy is used, the alloy is preferably a shape memory alloy of nickel and titanium. Preferably, the alloy comprises 10%-90% of titanium with the balance of nickel. The ratio of nickel to titanium preferably is in the range of 1:9-9:1, 2:8-8:2, 3-7-7:3, 4:6-6:4, or 5:5. Alternatively, the alloy is a nickel free shape memory alloy comprising other metallic and non-metallic elements that are able to perform shape memory effect and super-elasticity.

Both degradable and non-degradable shape memory polymers are known and can be used to make the devices. Suitable materials are described in U.S. Pat. Nos. 6,720,412, 6,388,043, and 6,160,084 to Lendlein and Langer. Polymeric materials are commercially available, for example, from Mnemo-Science GmbH, Germany.

Methods of Operation

In a preferred embodiment, the memory locking device is made of near-equiatomic nickel titanium (NiTi) alloy. After machining, the memory locking device receives a thermal treatment. With the thermal treatment, the memory locking device is able to close automatically by increasing the ambient temperature at or above the locking temperature, which is the temperature at or above the austenite phase transition starting temperature ($A_s$) (locking temperature). The memory locking device can however be re-opened again automatically if the ambient temperature is reduced to the unlocking temperature, which is the temperatures below the austenite phase transition starting temperature. The locking process can be triggered by direct or indirect heating, whereas the unlocking process can also be triggered by direct or indirect cooling.

When the temperature is below the locking temperature, the locking device is at a first configuration. In the first configuration shown in FIGS. 1A-1C, the diameter of the hole 9 is slightly greater than the outer diameter of spinal rod 12 because the shape-memory material is in its martensitic state. Thus, while the holding member is maintained in this first configuration, the spinal rod 12 is allowed to move within the hole 9.

As the temperature of the memory locking device is increased beyond the locking temperature, the shape-memory material shifts from its martensitic state to its austenitic state. In the austenitic state, the locking device is reformed into a second configuration in which the diameter of the hole 9 is reduced, contracting the spinal rod 12 such that the spinal rod 12 is not allowed to move within the hole 9. In another embodiment, the locking device may include an undercut at the bottom or side wall of the locking device in order to release the locking device. These devices are designed to re-tighten automatically if the device is being loosened in any condition such as fretting and wearing. The re-tightening effect is based on the super-elasticity and shape memory effect of shape memory materials.

The locking force of the locking device can be varied by adjusting the composition of the alloy, e.g., the content of nickel and titanium. Also, the locking force can be varied by different thermo-treatment, thermo-mechanical treatment, radiation treatment, ternary alloying, and any combination thereof. The treatments are normally under oxygen and pressure controlled environment. Alternatively, the locking force can be varied by adjusting the diameter, height, dimension, base thickness of the locking device.

The locking process is triggered by the means of direct or indirect heating, such as by conduction heating or the use of electromagnetic radiation. The locking/unlocking temperature of the locking device is adjustable by varying the composition of the alloy, e.g., the contents of nickel and titanium. It can also be varied by different thermo-treatment, thermo-mechanical treatment, radiation treatment, ternary alloying, and any combination thereof.

The locking/unlocking of the device can be triggered by any change of ambient temperature. The locking device can be locked by itself if the ambient temperature reaches the locking temperature, i.e., the austenite phase transition starting temperature. It can be released if the ambient temperature reaches the unlocking temperature, i.e., any temperature that is below the austenite phase transition starting temperature.

The device can reduce or prevent wear debris generation from the fretting occurring at the implant interface in order to minimize post-surgical complications in association with implant wear debris.

The present invention will be further understood by reference to the following non-limiting examples. The memory locking devices are described below in connection with the accompanying drawings. In the following discussion, same or similar elements are designated with the same numeral references and redundant description may be omitted.

EXAMPLE 1

Preparation of Sample

A shape memory locking device as described herein was made of near-equiatomic nickel titanium (Ti-50.8 wt % Ni) alloy. The mechanism then received a special heat treatment protocol ranging from 250° C. to 800° C., and from 30 minutes up to 60 minutes following the process described by Yeung et al., Materials Science and Engineering A 2004; 383(2):213-218. The locking temperature (above $A_s$) and unlocking (below $A_s$) temperatures of the memory locking device were programmed accordingly. The memory locking device can be closed when the ambient temperature is above the locking temperature, and loosened when the temperature is below the unlocking temperature.

For example, the shape memory locking device was first treated at 800° C. for 1 hr, followed by furnace cooling, and then treated at 500° C. for 0.5 hour, followed by water quenching. Eventually, its locking temperature was programmed at 35° C. or above, and the unlocking temperature was at 35° C. or below. This thermal treatment protocol is a non-limiting example of various thermal treatment protocols developed to adjust the locking and unlocking temperatures.

EXAMPLE 2

Comparative Testing

The performance of the memory locking device as depicted in FIGS. 1A-1C was tested against four conventional spinal couplings: 1. TSRH made of Ti-6Al-4V alloy (Medtronic, Sofamor Danek Company), 2. Moss Miami made of Ti-6Al-4V alloy (DePuy Spine, Johnson & Johnson Company), 3. CD-H made of Ti-6Al-4V alloy (Medtronic, Sofamor Danek Company) and 4. AO USS made of Ti-Al6-Nb7 alloy (Synthes® Company). The locking torque provided to secure the coupling device to the spinal rod was in accordance with the manufacturer recommendations.

Mechanical Testing

A Material Testing System (MTS) 858.02 Mini Bionix (USA) was used for mechanical testing of the samples. A customized testing jig for compression and torsion testing was attached to the MTS and connected to an external digital thermometer. The whole jig was immersed in a water bath to control the testing temperature. The ambient temperature was controlled by an external temperature-control heat circulator (Isotemp 2006S, Fisher Scientific, Pennsylvania, USA). This heat circulator provided a steady temperature environment at 37.5° C. (±0.5° C.) for the testing jig attached to the Material Testing System (MTS). The digital thermometer (HI92801C, Hanna, Portugal) was used to monitor the actual water temperature. The same setup was used in the tests of conventional spinal couplings.

The memory locking device described herein was embedded to the testing jig with the stem of the device perpendicular to the compression axis. One end of the spinal rod was connected to the memory locking device along the compression axis; while the other end was connected to the load cell of the MTS testing machine. The locking device of the memory device was triggered when the water bath temperature was raised beyond 37° C. After the locking device of the memory device was completed, the water bath temperature was reduced to 37° C.

The same setup was used for the mechanical testing of one of the conventional locking devices (AO USS). One end of the spinal rod 101 was connected to the screws 102 by the use of the coupling device 103, and the other end was then attached to the MTS load cell. Then, the coupling was tightened to secure the pedicle screw 102 and the spinal rod connection.

The testing protocols were described in ASTM F1798 standard and previous studies of mechanical testing of spinal instrumentation systems. See, Yeung et al., Materials Science and Engineering A 2004; 383(2):213-218; Magerl Clinical Orthopaedics 1984; 189:125-41; Kotani et al., Spine Jul. 15, 1999; 24(14):1406; Stanford et al., Spine Feb. 15, 2004; 29(4):367-375; Balabaud et al., Spine 2002; 27(17):1875-1880; and Glazer et al., Spine May 15, 1996; 21(10):1211-1222.

Axial Compression Test

Axial compression testing consists of two modes of loading; dynamic compression and static compression. Dynamic compression is applied by first preloading the coupling devices with a 350 N compressive load, and then applying a ±20 N dynamic load for five cycles. Static loading is applied with a compressive load on the coupling devices at the rate of 0.1 mm/sec, until the load reached 800 N or 1 mm displacement between the spinal rod and the coupling device is obtained, The load cell is then returned to its original position.

Axial Torsion Test

Axial torsion testing is applied to the coupling devices via the spinal rod attached to the MTS load cell. The testing is under angular displacement control to 20 and 40 degrees rotation. During the tests, the spinal rod is rotated by the load cell at a rate of 0.25 degree/sec. Once the load cell reaches the assigned degree of rotation, the cell is returned to the original position at the same rate. All data in the compression and torsion tests are recorded by the MTS machine. The data are analyzed by using student t-test for significance and the statistical analysis is performed using the SPSS program (SPSS for Windows, Release 11.0.0).

Testing Results

Figure 6:
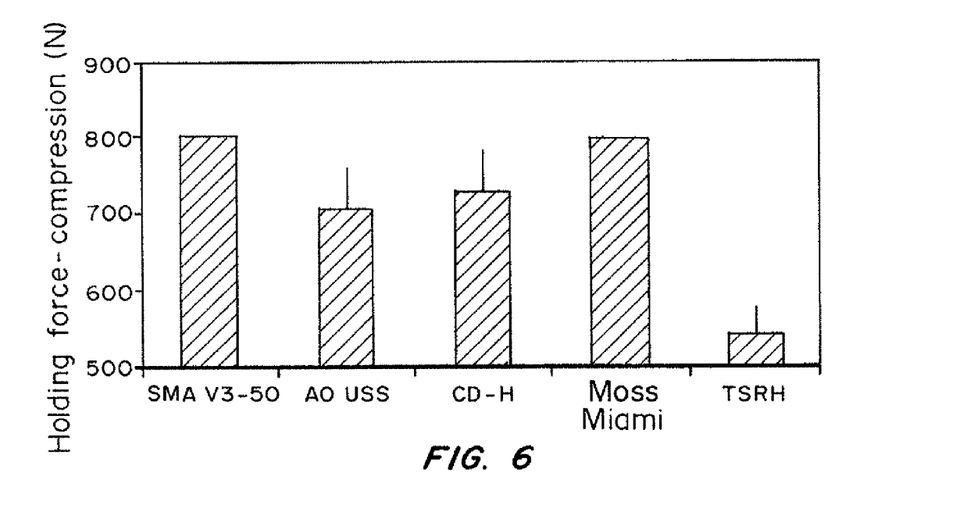
FIG. 6 is a graph of the holding force compression (N) for axial compression testing of samples.

FIG. 6 indicates the static compression testing results of one of the shape memory locking devices described herein ("SMA V3") together with the results for four conventional spinal couplings. The holding force is shown as a mean value±standard deviation. It was found that the holding forces of the memory locking device were higher than 800 N and prevented slippage. For the conventional couplings, the mean holding force of the Moss Miami samples was 800 N without slipping, while the mean holding force of AO USS samples was only 705 N. TSRH and CD-H samples slipped at 540 N and 728 N, respectively. The results demonstrate that the memory locking device locked tighter than the TSRH, CD-H and AO USS samples, and comparable to Moss Miami (MOSS) samples during axial compression.

Figure 7:
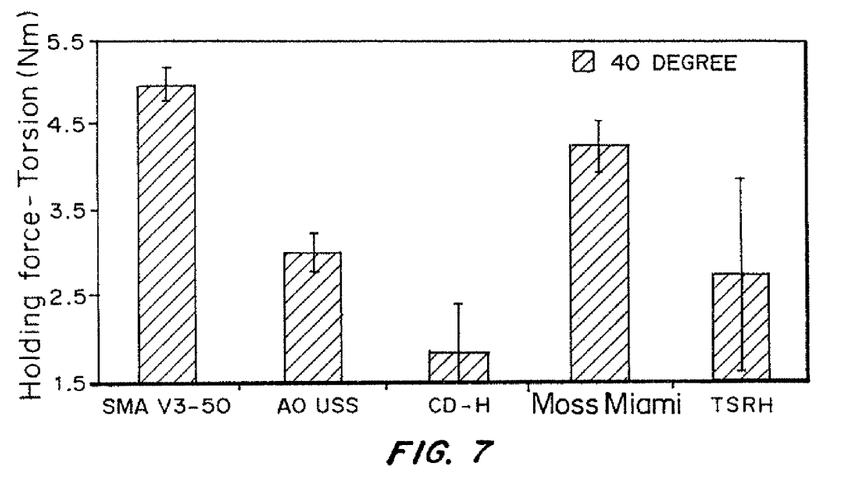
FIG. 7 is a graph of the holding force-Torsion (Nm) for axial torsion test of samples.
Figure 8:
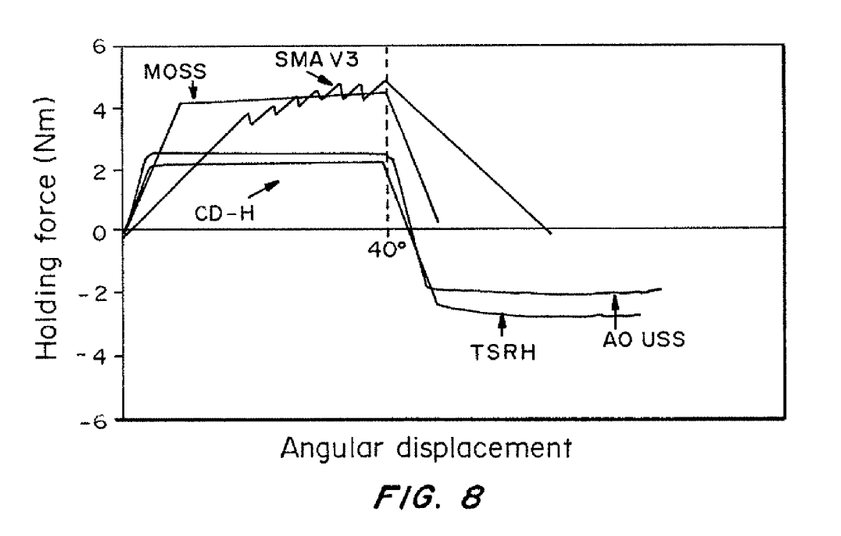
FIG. 8 is a graph showing the mechanical testing readout of the 40 degree axial rotation test of the samples, measured as the holding force (Nm) versus angular displacement

FIG. 7 indicates the axial rotation testing results for one of the memory locking devices and other conventional spinal couplings. The holding forces are shown as mean±standard deviation. For the 40 degree axial rotation test results, the maximum holding forces of the memory locking device was 5.0 Nm. The results for conventional memory locking devices showed the maximum holding forces of the AO USS, CD-H, Moss Miami and TSRH samples to be 3.0 Nm, 1.8 Nm, 4.25 Nm and 2.7 Nm, respectively. The axial torsion testing results demonstrated that the memory locking device was superior to all the conventional memory locking devices FIG. 8 shows the torsion—time relationship of one of the memory locking devices and conventional devices memory locking device for the 40 degree axial rotation test. Torque—time relationships of the couplings under 40 degree axial rotation testing. Line (a) represents the shape memory locking device described herein (SMA V3) at different angular displacements, line (b) represents the conventional spinal coupling CD-H, line (c) represents the conventional spinal coupling TSRH, line (d) represents the conventional spinal coupling AO USS, line (e) represents the conventional spinal coupling MOSS.

Slippage could be observed in all samples. When slippage occurred, the holding force of the conventional mechanisms would remain at a roughly constant value. In contrast, the shape memory device would alternate in a saw tooth pattern for the memory locking device as shown in the figure. The mechanical behavior of the memory locking device differed from that of other conventional mechanisms when slipping occurred, with the holding force increasing again immediately after slipping. This observation clearly demonstrates that the memory locking device has a re-tightening ability once the loosening or wearing occurs.

Modifications and variations of the present invention will be apparent to those skilled in the art and are intended to be encompassed by the following claims. All references cited herein are specifically incorporated by reference.

We claim:

1. A locking mechanism in an orthopedic implant formed of a shape memory super-elastic material having two-way shape memory, wherein the material is selected from the group consisting of metal alloys and polymers,
   wherein the locking mechanism locks when the ambient temperature is raised to 35° C. or greater and unlocks when the ambient temperature is reduced below 35° C., and
   wherein the locking mechanism automatically retightens after implantation in the event that loosening occurs, the retightening occurring without additional influence from energy external to the locking mechanism.

2. The locking mechanism of claim 1 wherein the shape memory material is a nickel-titanium alloy or nickel free alloy having shape memory and super-elasticity.

3. The locking mechanism of claim 2 comprising an alloy of 20-80% of nickel and 80-20% of titanium.

4. The locking mechanism of claim 1 wherein the locking mechanism is designed to receive a spinal rod and a sleeve assembly with the spinal rod.

5. The locking mechanism of claim 4 comprising a spline to enhance the locking security.

6. The locking mechanism of claim 4 comprising a low-profile design, a side-opening to allow capture or placement of the implant from the side, or an undercut at the bottom or side wall of the locking mechanism in order to release the locking mechanism.

7. The locking mechanism of claim 4 comprising an orthopedic implant to secure the head, spine, lower limb or upper limb.

8. The locking mechanism of claim 4 comprising
   a holding member, defining a hole for holding a spinal rod and at least one recess at the side of the hole facilitating expansion of the hole,
   a stem at the bottom of the holding member for forming into or connecting with a bone anchor,
   wherein the holding member allows movement of the spinal rod at one temperature and limits movement of the spinal rod at a different temperature.

9. The locking mechanism of claim 8, further comprising a spline at one side of the hole for enhancing the mechanical stability of the holding member and the security of the held spinal rod.

10. The locking mechanism of claim 8, wherein the stem is formed into a shape selected from a group consisting of screw, anchor, rod, shaft, and wire.

11. The locking mechanism of claim 8, wherein the holding member further comprises a top opening connecting with the hole for insertion of a tool.

12. The locking mechanism of claim 1 wherein the locking mechanism can form into or combine with a bone anchors such as a hook, pin, rivet or screw.

13. The locking mechanism of claim 1 wherein the locking force of the locking mechanism is adjustable by the selection of the composition, the dimensions of the locking mechanism or processing thereof.

14. The locking mechanism of claim 13 wherein the locking force is adjusted by thermo-treatment, thermo-mechanical treatment, radiation treatment, ternary alloying, or a combination thereof.

15. The locking mechanism of claim 13 wherein the locking force is adjusted by selection of the diameter, base thickness or height of the locking mechanism.

16. The locking mechanism of claim 1 wherein the locking mechanism comprises of near-equiatomic nickel-titanium alloy and the locking temperature of 35° C. is set by a heat treatment protocol comprising treatment at 800° C. for 1 hr, followed by furnace cooling, and then treatment at 500° C. for 0.5 hour, followed by water quenching.

17. A method of locking a prosthetic implant comprising:
providing a locking mechanism comprising a shape memory super-elastic material having two-way shape memory selected from the group consisting of metal alloys and polymers, wherein the locking mechanism locks to the prosthetic implant in a first shape and loosens in a second shape; and
securing the locking mechanism to the prosthetic implant in the first shape;
wherein the locking mechanism assumes the first shape when the ambient temperature is raised to 35° C. or greater and the second shape when the temperature is reduced below 35° C., and
wherein the locking mechanism automatically retightens due to the super-elasticity of the material in the event that loosening occurs after implantation, the retightening occurring without additional influence from energy external to the locking mechanism.

18. The method of claim 17 wherein the retightening of the prosthetic implant within the locking mechanism after implantation occurs without changing the temperature of the locking mechanism.

* * * * *